(12) United States Patent
Davis et al.

(10) Patent No.: US 6,440,375 B1
(45) Date of Patent: Aug. 27, 2002

(54) SUPER-ABSORBENT INSTRUMENT TRAYLINER FOR STERILIZATION PROCESS AND METHOD OF STERILIZING SURGICAL INSTRUMENTS

(75) Inventors: Phillip Davis, Weston; Vito L. DiPinto, South Windsor, both of CT (US)

(73) Assignee: General Hospital Supply Corporation, Wilton, CT (US)

( * ) Notice: Subject to any disclaimer, the term of this patent is extended or adjusted under 35 U.S.C. 154(b) by 0 days.

(21) Appl. No.: 09/686,453

(22) Filed: Oct. 11, 2000

Related U.S. Application Data

(60) Provisional application No. 60/158,779, filed on Oct. 12, 1999.

(51) Int. Cl.[7] ................................................. A61L 2/20
(52) U.S. Cl. ........................ 422/300; 422/292; 422/28; 206/438; 206/370
(58) Field of Search ........................... 422/300, 26, 28, 422/34, 292; 128/296, 287, 290 R; 521/159; 206/370, 438

(56) References Cited

U.S. PATENT DOCUMENTS

| | | | | |
|---|---|---|---|---|
| 3,566,871 A | * | 3/1971 | Richter et al. | 128/296 |
| 3,814,101 A | | 6/1974 | Kozak | |
| 4,023,570 A | * | 5/1977 | Chinai et al. | 128/290 R |
| 5,009,653 A | | 4/1991 | Osborn, III | |
| 5,164,421 A | * | 11/1992 | Kiamil et al. | 521/159 |
| 5,635,134 A | * | 6/1997 | Bourne et al. | 422/26 |

OTHER PUBLICATIONS

Absorbent Tray Liner, Kimberly–Clark, 1996.*

* cited by examiner

Primary Examiner—Robert J. Warden, Sr.
Assistant Examiner—Sean E. Conley
(74) Attorney, Agent, or Firm—Law Office of Roger C. Phillips

(57) ABSTRACT

The present invention is directed to a super-absorbent trayliner for use in a sterilization process and, more particularly, to a super-absorbent trayliner for cushioning surgical instruments and providing an advantageous moisture absorption functionality during and after completion of a sterilization process. The super-absorbent trayliner functions advantageously with steam or ethylene oxide gas as the sterilization agent. The super-absorbent trayliner is fabricated from a material having a desired level of moisture absorption, e.g., on the order of at least about thirty percent (30%) by dry weight, and is preferably fabricated from a hydrophilic polymeric foam material, e.g., a hydrophilic polyurethane foam. The disclosed super-absorbent trayliner may be advantageously utilized in sterilizing surgical instruments such that potential residual moisture is eliminated from the surface of the sterilized surgical instruments.

22 Claims, 1 Drawing Sheet

SUPER-ABSORBENT INSTRUMENT TRAYLINER FOR STERILIZATION PROCESS AND METHOD OF STERILIZING SURGICAL INSTRUMENTS

CROSS-REFERENCE TO RELATED APPLICATIONS

The present application claims benefit of co-pending provisional patent application, Ser. No. 60/158,779, filed Oct. 12, 1999, the contents of which are incorporated herein by reference.

BACKGROUND

1. Technical Field

The present invention relates to trayliners for use in a sterilization process and, more particularly, to a super-absorbent trayliner for cushioning surgical instruments and providing an advantageous moisture absorption functionality during and after completion of a sterilization process. In a preferred embodiment of the present invention, a super-absorbent, foam plastic trayliner is disclosed for cushioning surgical instruments and providing an advantageous moisture absorption functionality during and after sterilization procedures that utilize steam and/or ethylene oxide gas as a sterilization agent.

2. Background of the Related Art

As is well known, surgical instruments used in the healthcare industry must be sterilized before and after each use. Sterilization, of course, frees instruments from microorganism contamination, to prevent infections and the spread of diseases among patients. All medical procedures rely upon a stringent program of sterilization.

The medical device industry has addressed the sterilization requirements in the surgical field by offering two general types of surgical instruments: reusable instruments and single use, or disposable, instruments. Reusable instruments are typically composed of stainless steel and are typically sterilized before their initial use and then cleaned and resterilized prior to each subsequent use thereof. Single use or disposable instruments, on the other hand, are often fabricated primarily from plastic materials, thereby reducing costs associated with manufacture, and are discarded after use in a single procedure.

With respect to reusable surgical instruments, e.g., forceps, graspers, dissectors, probes, hemostats, scissors and the like, historically sterilization and resterilization have been accomplished using two primary sterilization modalities: steam sterilization and ethylene oxide sterilization. Of the two primary sterilization modalities, steam sterilization has been the overwhelmingly dominant method of sterilization in the surgical instrument field.

In a broad sense, the sterilization process generally involves placing instruments to be sterilized in a tray, wrapping the instruments and the tray with a sterilization wrap, and placing the wrapped tray and instruments in a sterilization chamber where the instruments are exposed to the sterilization medium of either steam or ethylene oxide. Preferably, the instruments are placed in a tray and wrapped before initiating exposure to the sterilization medium. Wrapping the tray generally contributes to providing a level of protection to the surgical instruments, e.g., during post-sterilization storage and handling prior to actual use, and to maintaining the instruments in a dry, sterile condition. Typically, sterilization trays are wrapped with a sterilization wrap, e.g., paper. Other instruments to be sterilized include basins. Basins are separated by cotton towels or other absorbent materials and then wrapped in sterilization wrap prior to sterilization.

One long and continuing problem encountered with steam and/or ethylene oxide sterilization, however, is the presence of moisture that remains on the implements such as on sterilized instruments, i.e., within the sterile wrap, at the conclusion of the sterilization process. This residual moisture can range from slight levels of dampness to visible droplets on the surface of surgical instruments. Such residual moisture is both undesirable and is unacceptable because such moisture could permit migration of surface microorganisms, thereby penetrating the wrapped tray and rendering its contents contaminated.

A wrapped tray with residual moisture has been termed a "wet pack," i.e., a wrapped tray containing surgical instruments having surface moisture on the inside and/or outside of the wrapped tray, e.g., during and after the sterilization process. In one of its marketing publications, Getinge/Castle, Inc. of Rochester, N.Y., a major manufacturer of sterilizers, refers to the "wet pack" problem as "an age old predicament." Wet pack problems may be caused and/or exacerbated by, e.g., the use of new sterilizers, boiler or plumbing changes or even ambient humidity variations due to air conditioning, etc. What is needed, therefore, is a more effective means than, e.g., a paper or cotton product for preventing the "wet pack" problem and the resulting potential for contamination of sterilized surgical instruments.

SUMMARY OF THE DISCLOSURE

According to the present invention, a highly absorbent trayliner is provided that may be advantageously placed in a sterilization tray, e.g., along the tray bottom, to absorb potential residual moisture generated during the sterilization process. The highly absorbent trayliner advantageously maintains surgical instruments positioned in the wrapped tray in a "dry" condition at the completion of the sterilization process and further cushions the instrumentation, thereby minimizing the potential for instrument damage during post-sterilization handling. The highly absorbent trayliner of the present invention is preferably compatible with a steam or ethylene oxide sterilization process.

In addition, the trayliner of the present invention advantageously neither interferes with nor inhibits conventional steam and ethylene oxide sterilization procedures. Thus, the super absorbent trayliner of the present invention permits air removal, sterilant penetration/evacuation, drying and effective aeration of instruments that are sterilized according to conventional steam or ethylene oxide sterilization procedures. Moreover, the instrument trayliner of the present invention is advantageously lint-free, preferably pre-cut to fit standard sterilization trays or other surgical instruments, and relatively inexpensive such that disposal of the trayliner after a single use is cost effective for sterilization operators.

The super-absorbent sterilization trayliner may be advantageously utilized in a sterilization method to achieve superior results, particularly in terms of reduced residual moisture on the surface(s) of surgical instrument(s). A sterilization method according to the present invention generally includes placing a trayliner in the bottom of a sterilization tray, placing one or more instruments on top of the trayliner, wrapping the tray in a sterilization wrap to form a pack, and then sterilizing the pack with steam or ethylene oxide.

In a preferred embodiment of the present invention, a super-absorbent trayliner is fabricated from a material that is moisture absorbent, i.e., hydrophilic, and preferably a material that absorbs moisture up to about thirty percent (30%) of its weight. Trayliners fabricated from materials having moisture absorbency at a level as described herein have been found to achieve beneficial results, e.g., prevent residual moisture on instrument surfaces post-sterilization, and allow effective operation of conventional steam and ethylene oxide processes. A preferred material for use in fabricating a super-absorbent trayliner according to the present invention is a hydrophilic polyurethane foam available from Foamex International, Inc. (Linwood, PA) under the tradename Aquazone®.

In sum, a super-absorbent trayliner and a method of sterilization according to the present invention, have been found to reduce "wet pack" problems associated with the sterilization of surgical instruments. Still other features and advantages of the presently disclosed super-absorbent sterilization trayliner and method for sterilizing surgical instruments will become apparent upon reading the following detailed description in conjunction with attached drawings.

BRIEF DESCRIPTION OF THE DRAWINGS

So that those having ordinary skill in the art to which the disclosed trayliner and associated method appertains will more readily understand how to employ and use the same, reference may be had to the drawings wherein.

DETAILED DESCRIPTION OF PREFERRED EMBODIMENT(S)

Referring to the attached drawings, a super-absorbent trayliner 10 is provided for introduction into a sterilizing system in connection with the sterilization process. The super-absorbent trayliner 10 of the present invention advantageously functions to prevent the presence of residual moisture on the surface of surgical instruments at the conclusion of the sterilization process by absorbing such potential residual moisture. The super-absorbent trayliner 10 of the present invention further advantageously cushions surgical instruments to be sterilized, e.g., forceps, graspers, dissectors, probes, hemostats, scissors and the like, both during and after a sterilization process. Trayliner 10 is preferably fabricated from a hydrophilic polyurethane foam that absorbs on the order of thirty percent (30%) by dry weight and is adapted for use in sterilization processes that utilize steam or ethylene oxide as the sterilizing agent. A particularly preferred material for use in fabricating super-absorbent trayliner 10 is Aquazone® polyurethane foam.

Figure 1:
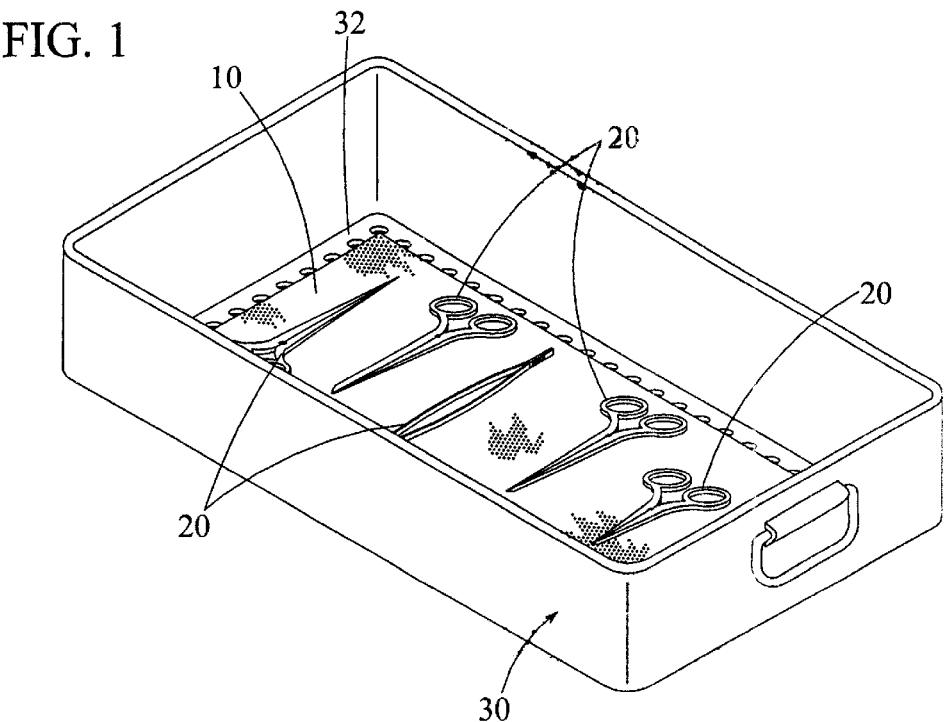
FIG. 1 shows a perspective view of a trayliner according to the present invention, lying beneath surgical instruments within a sterilization tray.

With reference to FIG. 1, super-absorbent trayliner 10 generally comprises a sheet of super-absorbent material cut to substantially cover a base 32 of a sterilization tray 30. The base 32 of the sterilization tray 30 may be solid or perforated, as is known in the art. As shown, super-absorbent trayliner 10 is of rectangular configuration; however, alternative geometries are contemplated, e.g., as may be appropriate for specific sterilization tray configurations. Super-absorbent trayliners may be dimensioned depending upon the application. Preferred super-absorbent trayliners 10 measure approximately 12×12, 12×14, 12×16, 12×18, 12×20 and 12×22 inches, respectively, and are approximately ⅛th inch in thickness. Trayliners 10 preferred for use in separating basins measure approximately 3×24 inches and may also be ⅛ inch in thickness.

Preferably, the super absorbent trayliner 10 is fabricated from a non-woven, lint free material that is compatible with both steam and ethylene oxide sterilization. The super-absorbent trayliner 10 preferably is fabricated from a hydrophilic polymeric foam plastic, e.g., a hydrophilic polyurethane foam. The super absorbent trayliner 10 preferably absorbs on the order of at least about thirty percent (30%) by dry weight. A specific foam plastic suitable for use is a non-reticulated polyurethane ester foam available from Foamex Corporation (www.foamex.com) under the tradename Aquazone® foam. The Aquazone® foam absorbs moisture of approximately thirty three percent (33%) by dry weight.

The typical physical properties of the Aquazone® foam include the following:

| | |
|---|---|
| Foam type: | Polyurethane Ester Foam |
| Reticulation: | None |
| Pore Size (ppi): | 85 |
| Density (lbs/ft³): | 1.8 |
| Wet tensile (psi): | 25 |
| Dry tensile (psi): | 30 |
| Dry tear (pli): | 4.2 |
| Wet elongation (%): | 480 |
| Dry elongation (%): | 400 |
| 25% CFD (psi): | 0.56 |
| 65% CFD (psi): | 0.81 |
| 58% Compression Set (%): | 11 |
| Water-holding (% dry weight): | 33 |
| Wet-out (sec): | <10 |
| Volume swell (%): | 3 |
| 2 min H₂O capillary height (cm) | 2.5 |

The super-absorbent trayliner 10 of the present invention is particularly adapted for use in a steam sterilization system or ethylene oxide sterilization system. As is known, a sterilization system generally includes a sterilization chamber that is adapted to receive instruments to be sterilized, and a source of a sterilizing agent, e.g., steam or ethylene oxide, connected to the sterilization chamber.

Figure 2:
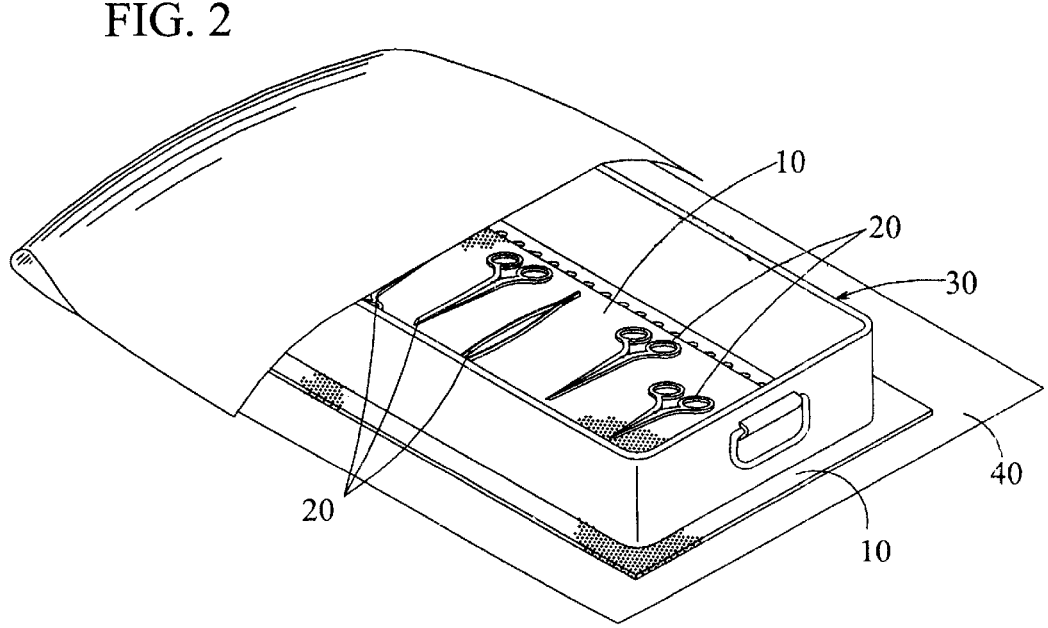
FIG. 2 shows a perspective view of an alternative trayliner embodiment according to the present invention, positioned under the sterilization tray of FIG. 1, with a sterilization wrap positioned therearound.

A preferred method for sterilizing surgical instruments 20 according to the present invention includes positioning the trayliner 10 in the base of the tray 30, as shown in FIGS. 1 and 2, and positioning instruments 20 on the trayliner. The types of instruments 20 that may benefit from the sterilization method disclosed herein includes all conventional surgical instruments, particularly reusable surgical instruments composed of stainless steel. Determinations as to the types of surgical instruments 20 to be placed on tray 30, the numbers/weights of such surgical instruments, the spacing of such surgical instruments, sterilization cycles, and the like, are made according to conventional sterilization criteria. Although not, shown, a trayliner 10 could also be placed on top of the instruments to provide further absorption capabilities to the system, as will be apparent to persons skilled in the art.

As shown in the alternative embodiment of FIG. 2, tray 30 contains super-absorbent trayliner 10 and a plurality of instruments 20 positioned thereon. Tray 30 is then advantageously wrapped in a conventional sterilization wrap 40.

Sterilization wrap 40 may be fabricated from paper and, optionally, a second super-absorbent trayliner 10 or other cushioning member may be placed between tray 30 and sterilization wrap, thereby reducing the risk that wrap 40 may be torn by the corners of tray 30. Once wrapped in the sterilization wrap 40, tray 30 is ready to be placed in a sterilization unit for sterilization of surgical instruments 20. At the conclusion of the sterilization cycle, tray 30 is typically removed from the sterilization unit (not pictured), and the sterilized instruments 20 are, in due course, removed from the tray and made ready for subsequent surgical procedures. At the conclusion of the sterilization cycle, the super-absorbent trayliner 10 of the present invention is typically disposed of in a conventional waste container.

The super-absorbent trayliner of the present invention provides significant benefits to the reliability and efficacy of conventional sterilization operations. Ideally, as is known in the art, when the sterilization system is operating at peak performance a sterilization system that utilizes steam or ethylene oxide as the sterilizing agent will be totally dry at the conclusion of the sterilization cycle. However, as discussed above due to ambient humidity, plumbing, etc., sterilization systems are highly variable in operation and such systems do not always operate at peak levels. As a result, without use of a super-absorbent trayliner 10, it is not uncommon for residual moisture to be found on the surface of sterilized instruments at the conclusion of the sterilization cycle. The super-absorbent tray-liner of the present invention exhibits sufficient hydrophilicity to absorb an amount of moisture sufficient to address typical operative variability.

Trayliners according to the present invention have been tested to ascertain their effectiveness in absorbing moisture, i.e., removing any potential residual moisture from the surface of sterilized instruments. Results of a water capacity test on a polyurethane foam in accordance with the present invention along with those of a cotton towel are provided in TABLES 1 and 2. It will be recognized that such a test for water capacity may be found in the text entitled "Design and Applications of Hydrophilic Polyurethanes", by T. Thomson, Technomic Publishing Company, Inc., 2000, which is hereby incorporated herein by reference. These tests have verified the efficacy of the super-absorbent trayliners of the present invention.

TABLE 1

| LINER | | % WATER CAPACITY | % DRAINED WATER CAPACITY |
|---|---|---|---|
| Dry Weight | 14.22 g | | |
| Soaked Weight | 372.00 g | 2,616% | 1,460% |
| Drained Weight | 207.66 g | | |

TABLE 2

| COTTON TOWEL | | % WATER CAPACITY | % DRAINED WATER CAPACITY |
|---|---|---|---|
| Dry Weight | 96.10 g | | |
| Soaked Weight | 445.95 g | 464% | 302% |
| Drained Weight | 289.75 g | | |

These results reveal that the water capacity of a super-absorbent tray liner of the present invention is significantly higher than that of a cotton towel. Accordingly, during the sterilization process, the tray liner 10 will absorb significantly more moisture that has condensed on surgical instruments than cotton towel will absorb.

Super-absorbent trayliners of the present invention along with cotton towels were also tested for moisture content after completion of the sterilization process to determine whether they had adequately dried during the drying cycle. The results showed that each of the inventive trayliners had completely dried. These results are provided in TABLE 3.

TABLE 3

| | ABSORBENT INSTRUMENT TRAY LINER | | | COTTON TOWEL | | |
|---|---|---|---|---|---|---|
| GRAVITY 132° C. | PRE WEIGHT | POST WEIGHT | MOISTURE RETENTION | PRE WEIGHT | POST WEIGHT | MOISTURE RETENTION |
| Run 1 | 12.67 g | 12.45 g | −1.77% | 99.77 g | 99.67 g | −0.10% |
| Run 2 | 12.85 g | 12.67 g | −1.42% | 103.68 g | 102.62 t | −1.03% |
| Run 3 | 12.83 g | 12.69 g | −1.10% | 100.22 g | 98.28 g | −1.97% |

The present invention, therefore, provides a super-absorbent trayliner 10 that functions to cushion surgical instruments in connection with the sterilization process, and further functions to absorb potential excess moisture that might remain on the surgical instruments at the conclusion of a steam or ethylene oxide sterilization process. The super-absorbent trayliner has been found to permit proper air removal, sterilant penetration/evacuation, and delivery of sterilized surgical instruments substantially devoid of residual moisture at the conclusion of a sterilization process. The super-absorbent trayliner has also been found to permit effective aeration of instruments sterilized with ethylene oxide.

The principles, preferred embodiments and modes of operation of the presently disclosed super-absorbent instrument trayliner and method of sterilizing surgical instruments have been described in the foregoing specification. The presently disclosed super-absorbent instrument trayliner and method of sterilization, however, are not to be construed as limited to the particular embodiments shown as these embodiments are regarded as illustrious rather than restrictive. Moreover, variations and changes may be made by those skilled in the art without departing from the spirit of the presently disclosed super-absorbent instrument trayliner and method of sterilization.

What is claimed is:

1. A sterilization trayliner for use in a sterilization cycle of a sterilizer during which at least one medical instrument is sterilized by a sterilization agent, comprising:

a sheet of a planar material comprising a hydrophilic polymeric foam and being dimensioned and configured to fit within a sterilization tray, the sheet being used during the sterilization cycle whereby the sheet absorbs residual sterilization agent from the at least one medical instrument during one portion of the sterilization cycle and thereafter provides aeration for drying of the at least one medical instrument during another portion of the sterilization cycle.

2. A sterilization trayliner according to claim 1, wherein said sheet comprises a hydrophilic polyurethane foam.

3. A sterilization trayliner according to claim 1, wherein said sheet comprises a hydrophilic polymeric foam that absorbs moisture of at least about thirty percent by dry weight.

4. A sterilization trayliner according to claim 1, wherein said sheet comprises a hydrophilic polyurethane foam that is non-reticulated.

5. A sterilization trayliner according to claim 1, wherein said sheet comprises a non-reticulated and hydrophilic polyurethane ester foam for cushioning surgical instruments placed thereon during a sterilization procedure.

6. A sterilization trayliner according to claim 1, wherein said sheet is approximately 1/8 inch in thickness.

7. A sterilization trayliner according to claim 1, wherein said sheet comprises a hydrophilic polymeric foam that has a water capacity of greater than approximately 2000% by dry weight.

8. A sterilization trayliner according to claim 7, wherein said sheet is fabricated from a hydrophilic foam plastic that has a water capacity of approximately 2,616% by dry weight.

9. A method for sterilizing surgical instruments during a sterilization cycle, comprising the steps of:

(a) providing a sterilization trayliner fabricated from a hydrophilic polyurethane foam;

(b) placing the sterilization trayliner on the base of a sterilization tray;

(c) positioning at least one surgical instrument on the sterilization trayliner; and (d) introducing a sterilizing agent to the sterilization tray to sterilize said at least one surgical instrument whereby the trayliner absorbs residual sterilization agent form said at least one surgical instrument during one portion of the sterilization cycle and thereafter provides aeration for drying of said at least one instrument during another portion of the sterilization cycle.

10. A method according to claim 9, wherein said sterilization trayliner is fabricated from a hydrophilic polyurethane foam.

11. A method according to claim 9, wherein said sterilization trayliner is fabricated from a hydrophilic polymeric foam plastic that absorbs moisture of at least about thirty percent by dry weight.

12. A method according to claim 9, wherein said sterilization trayliner is fabricated from a hydrophilic polyurethane foam that is non-reticulated.

13. A method according to claim 9, wherein said sterilization trayliner is fabricated from a non-reticulated and hydrophilic polyurethane ester foam for cushioning surgical instruments placed thereon during a sterilization procedure.

14. A method according to claim 9, wherein said sterilization trayliner is approximately 1/8 inch in thickness.

15. A method according to claim 9, wherein said sterilizing agent is selected from steam and ethylene oxide.

16. A method according to claim 9, further comprising placing a second sterilization trayliner on top of said at least one surgical instrument prior to introducing the sterilizing agent.

17. A method according to claim 16, wherein said second sterilization trayliner is fabricated from a hydrophilic polyurethane foam.

18. A method according to claim 9, further comprising wrapping the sterilization tray with a wrap prior to introducing the sterilizing agent.

19. A method according to claim 18, wherein said wrap comprises paper.

20. A method according to claim 19, wherein said sterilization trayliner functions to remove potential residual moisture from the surface of said at least one surgical instrument.

21. A method according to claim 9, wherein said sterilization trayliner functions to cushion said at least one surgical instrument.

22. A method according to claim 21, wherein said sterilization trayliner is fabricated from a hydrophilic foam plastic that has a water capacity of approximately 2,616% by dry weight.

* * * * *

UNITED STATES PATENT AND TRADEMARK OFFICE
CERTIFICATE OF CORRECTION

PATENT NO.     : 6440,375 B1
DATED          : August 27, 2002
INVENTOR(S)    : Phillip Davis and Vito L. DiPinto It is certified that error appears in the above-identified patent and that said Letters Patent is hereby corrected as shown below:

Title page,
Item [54], in the title of the invention please delete "SUPER-".

Item [57], ABSTRACT,
Line 1, delete "The present invention is directed to a super-"
Line 1, change "absorbent" to read -- An absorbent --.
Lines 2 -4, delete "and, more particularly, to a super-absorbent trayliner for cushioning surgical instruments and providing" and insert -- provides -- therefor.
Line 5, delete "functionality" and insert -- and drying capability -- therefor.
Line 6, delete "super-".
Lines 6 and 7, delete "functions advantageously" and insert -- may be employed -- therefor.
Line 8, delete "super-".
Line 8, delete "is" and insert -- may be -- therefor.
Line 13, delete "disclosed super-".

Column 1,
Line 1, delete "SUPER-".
Line 17, change "a super-" to read -- an --.
Line 21, change "a super-" to read -- an --.

Column 2,
Line 47, delete "super".
Line 56, delete "super-".
Lines 66 and 67, change "a super-" to read -- an --.

Column 3,
Lines 8 and 9, change "a super-" to read -- an --.
Line 13, change "a super-" to read -- an --.
Line 17, delete "a super-".
Line 40, change "a super-" to read -- an --.
Line 47, delete "a super-".
Line 56, delete "a super-".
Line 59, delete "super-".
Line 60, delete "super-".
Line 63, delete "super-".
Line 66, delete "super-".

UNITED STATES PATENT AND TRADEMARK OFFICE
CERTIFICATE OF CORRECTION

PATENT NO. : 6440,375 B1
DATED : August 27, 2002
INVENTOR(S) : Phillip Davis and Vito L. DiPinto It is certified that error appears in the above-identified patent and that said Letters Patent is hereby corrected as shown below:

<u>Column 4,</u>
Line 1, delete "super".
Line 7, delete "super".
Line 10, delete "super".
Line 13, delete "super".
Line 40, delete "super-".
Line 65, delete "super-".

<u>Column 5,</u>
Line 2, delete "super-".
Line 13, delete "super-".
Line 25, delete "super-".

<u>Column 6,</u>
Line 23, change "super-absorbent" to read -- Absorbent --.
Line 42, delete "super-".
Line 48, delete "super-".
Line 52, delete "super-".
Line 48, delete "super-".
Line 57, delete "super-".
Line 60, delete "super-".
Line 66, delete "super-".

Signed and Sealed this

Seventh Day of January, 2003

JAMES E. ROGAN
*Director of the United States Patent and Trademark Office*